US00PP21180P3

(12) United States Plant Patent
Alamo et al.

(10) Patent No.: US PP21,180 P3
(45) Date of Patent: Aug. 3, 2010

(54) BLUEBERRY PLANT NAMED 'SEVILLA'

(50) Latin Name: *Vaccinium corymbosum L.*
Varietal Denomination: Sevilla

(75) Inventors: Antonio Abad Alamo, Huelva (ES); José Ulf Hayler López, Huelva (ES); Paul M. Lyrene, Micanopy, FL (US)

(73) Assignee: Royal Berries S.L., Almonte, Huelva (ES)

( * ) Notice: Subject to any disclaimer, the term of this patent is extended or adjusted under 35 U.S.C. 154(b) by 0 days.

(21) Appl. No.: 12/289,432

(22) Filed: Oct. 28, 2008

(65) Prior Publication Data

US 2009/0210983 P1 Aug. 20, 2009

(30) Foreign Application Priority Data

Feb. 14, 2008 (QZ) ..... PBR 2008/0337

(51) Int. Cl.
*A01H 5/00* (2006.01)

(52) U.S. Cl. ..... Plt./157

(58) Field of Classification Search ..... Plt./157
See application file for complete search history.

*Primary Examiner*—June Hwu
(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers and forms fruit at late-season. The attractive large light blue flattened-round berries exhibit an aromatic sweet flavor. It is recommended that the plant be grown in dry climates outside tunnels. The plant commonly requires cross pollination, and displays a generally open-round somewhat sprawling growth habit with attractive foliage that commonly defoliates during the winter. A low chilling requirement is also exhibited.

4 Drawing Sheets

Botanical/commercial classification *Vaccinium corymbosum* L. /Blueberry Plant.
Varietal denomination cv. Sevilla.

SUMMARY OF THE INVENTION

The new Blueberry cultivar of the present invention was the product of controlled artificial pollination carried out in a greenhouse at Greenwood, Fla., U.S.A., wherein two parents were crossed during 1998 which previously had been studied in the hope that they would contribute the desired characteristics. The female parent (i.e., the seed parent) was the unreleased 'FL 98-19' cultivar (non-patented in the United States). The male parent (i.e., pollen parent) was the 'Millennia' cultivar (U.S. Plant Pat. No. 12,816). The parentage of the new cultivar can be summarized as follows:

'FL 98-19'×'Millennia'.

The seeds resulting from the pollination were shipped to Almonte, Huelva, Spain, where they sown during approximately 1999, small plants were obtained which were physically and biologically different from each other and selective research of the progeny was carried out. Selective study during the spring of 2003 resulted in the identification of a single plant of the new cultivar. This plant initially was designated S03-08-04.

It was found that the new Blueberry plant of the present invention displays the following combination of characteristics:

(a) flowers and forms fruit at late-season,
(b) displays a generally open-round somewhat sprawling growth habit with attractive foliage that commonly defoliates during the winter,
(c) commonly requires cross pollination for a good fruit set and quality, (d) displays a low chilling requirement, and
(e) forms in abundance attractive large light blue flattened-round berries that exhibit an aromatic sweet flavor.

The new cultivar well meets the needs of the horticultural industry and can be grown to advantage for the commercial production of blueberries. The plant is recommended for growing in dry climates outside tunnels while using non-evergreen management.

The new cultivar of the present invention can be distinguished from all other Blueberry cultivars known to its originators. The 'FL 98-19' female parent plant is unreleased to the public and accordingly is not available to the public for use as a comparative cultivar. No comparative information is available concerning the distinguishing characteristics of the new cultivar when compared to the 'FL 98-19' parental cultivar. Also, since the 'FL 98-19' cultivar no longer exists, it is impossible to obtain such comparative information. The 'Millennia' male parent forms fewer flowers per cluster and smaller berries. When compared to the 'Misty' cultivar (non-patented in the United States), the 'Misty' cultivar forms considerably smaller berries of approximately 14 mm in diameter. When compared to the 'Star' cultivar (U.S. Plant Pat. No. 10,675), the 'Star' cultivar commonly displays a taller more upright growth habit, and is less susceptible to Stem Blight. When compared to the 'Sharpblue' cultivar (non-patented in the United States), the 'Sharpblue' cultivar displays evergreen foliage that is well retained during the winter, does not require cross-pollination, and is less resistant to aphids.

The new cultivar has been asexually reproduced by the rooting of cuttings beginning during the summer of 2003 at Almonte, Huelva, Spain. Such asexual propagation has shown that the characteristics of the new cultivar are firmly fixed and are stably transmitted from one generation to another. Accordingly, the new cultivar asexually reproduces in a true-to-type manner.

The new cultivar has been named 'Sevilla'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of softwood cuttings, and were being grown outdoors at Almonte, Huelva, Spain.

DETAILED DESCRIPTION

Figure 1:
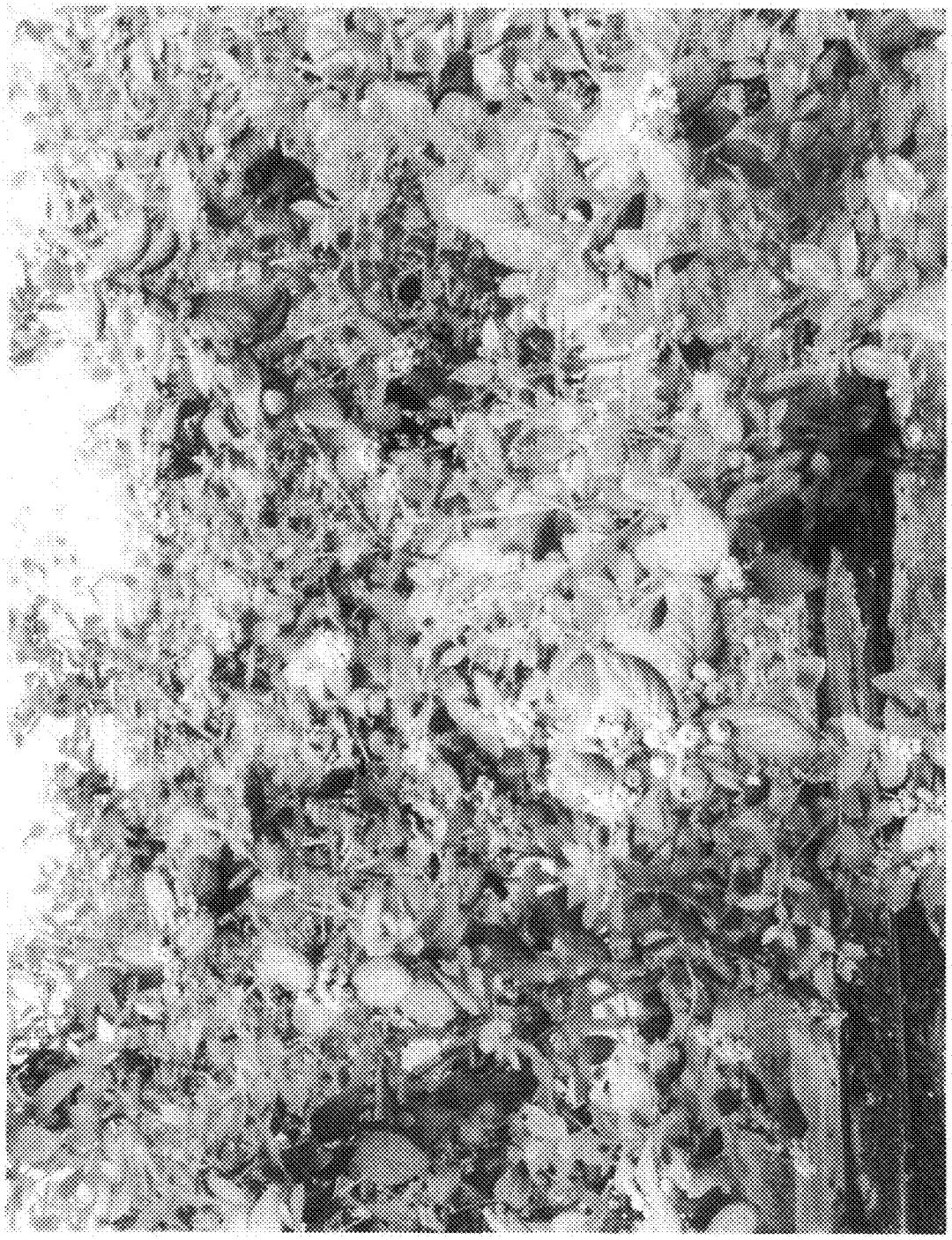
FIG. 1 shows an overall view of a typical fruiting plants of the new cultivar where the generally open-round somewhat sprawling growth habit is illustrated.
Figure 2:
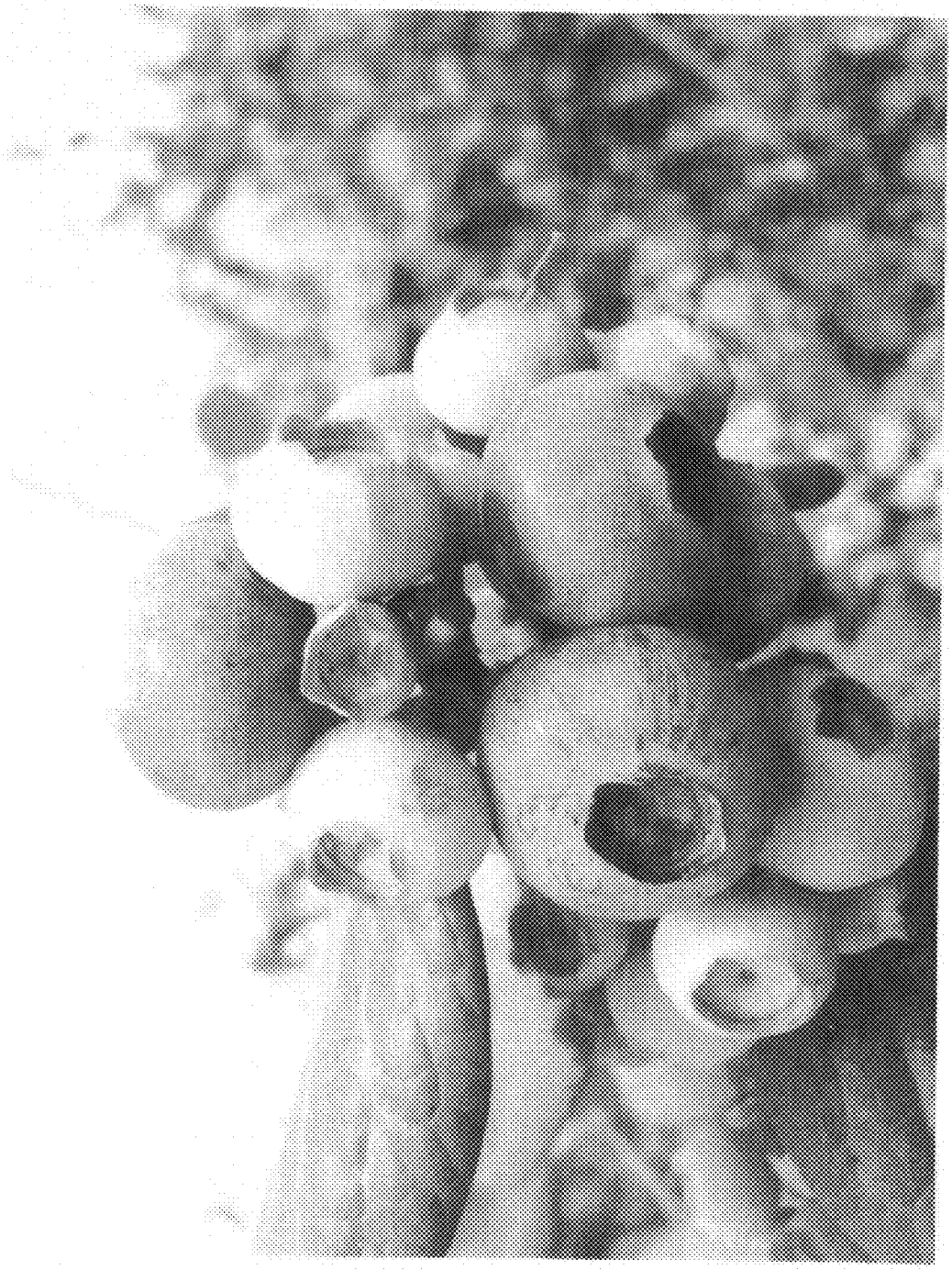
FIG. 2 shows typical berries of the new cultivar in various stages of maturity as well as the foliage.
Figure 3:
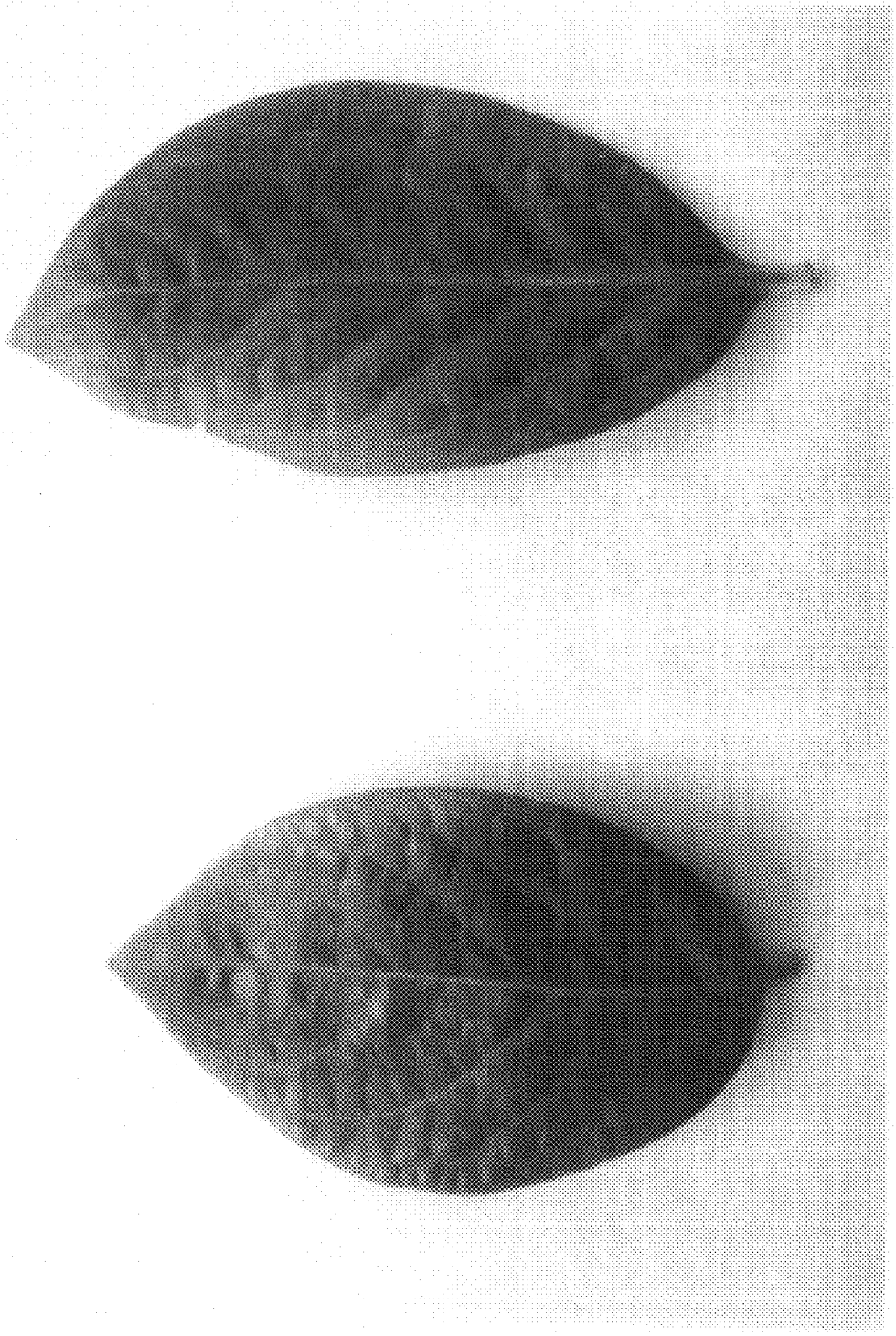
FIG. 3 shows the upper (adaxial) surfaces of typical leaves of the new cultivar.
Figure 4:
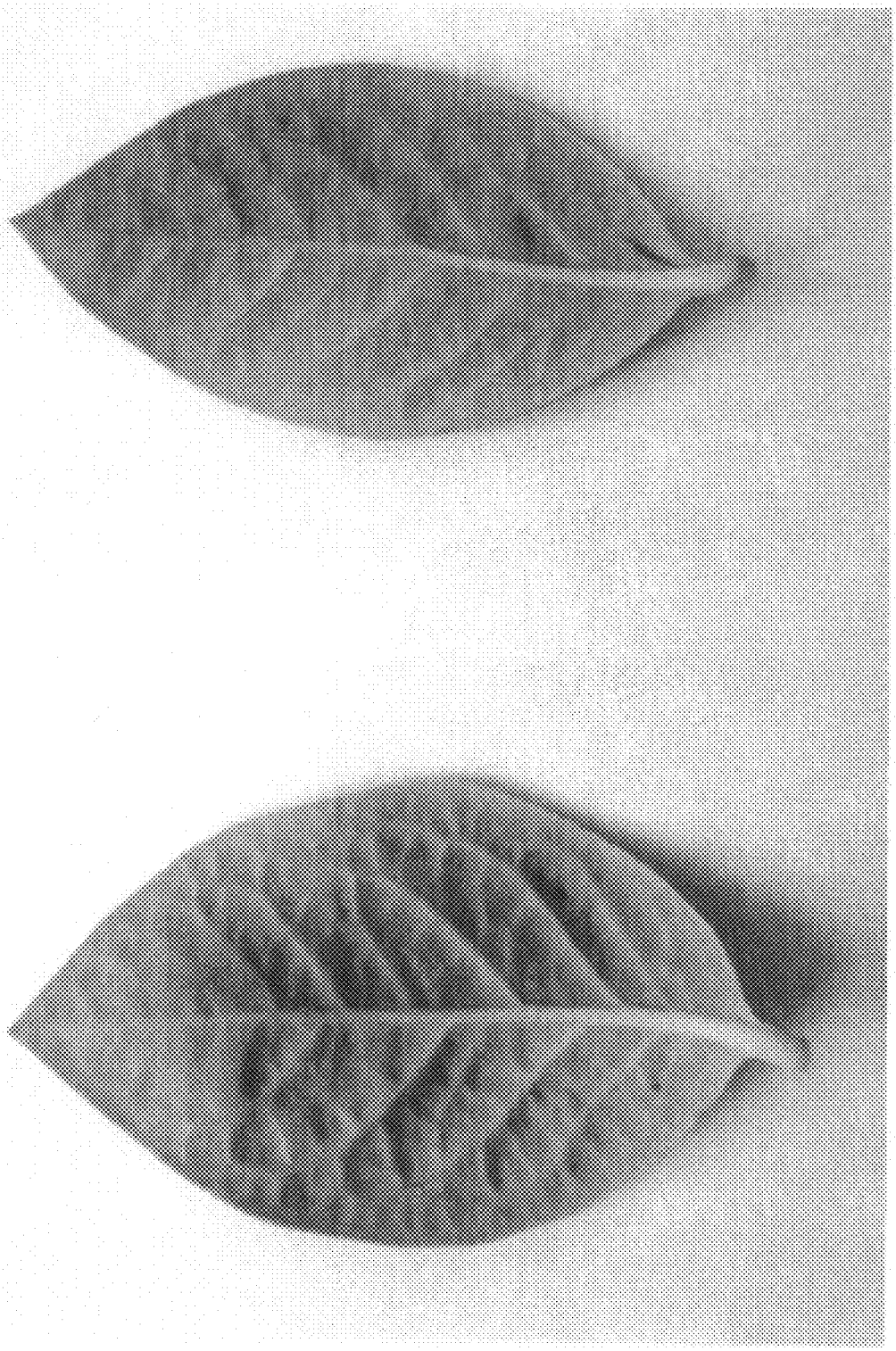
FIG. 4 shows the under (abaxial) surfaces of typical leaves of the new cultivar.

The chart used in the identification of the colors described herein is The R.H.S. Colour Chart of The Royal Horticultural Society, London, England. Ordinary color terms are to be accorded their customary dictionary significance. The description is based on the observation of approximately four-year-old plants of the new cultivar which had been asexually reproduced by the rooting of softwood cuttings while growing outdoors at Almonte, Huelva, Spain.

Plant:

*Growth habit.*—Generally open-round and semi-sprawling.

*Height.*—Approximately 1.7 m at 4 years of age.

*Width.*—Approximately 4.6 m at 4 years of age.

*Mature canes.*—Commonly approximately 58.2 cm in length on average, approximately 3.2 cm in diameter at the base on average, and approximately 2.2 cm in diameter towards the tip on average, and near Grey-Brown Group 199D in coloration.

*Foliage retention.*—Defoliates during the winter commonly with approximately 70 percent defoliation.

*Chill requirement.*—Less than approximately 300 hours.

Foliage:

*Shape.*—Generally elliptic (as illustrated).

*Length.*—Commonly approximately 61 mm on average.

*Width.*—Commonly approximately 37 mm on average.

*Apex.*—Acute.

*Base.*—Acute.

*Margin.*—Entire.

*Texture.*—Glabrous and non-glandular on both surfaces.

*Color.*—Green Group 137C on the upper (adaxial) surface, and Green Group 138B on the under (abaxial) surface.

*Petiole.*—Commonly approximately 4.8 mm in length on average, commonly approximately 2 mm in diameter on average, and near Yellow-Green Group 145B in coloration on both surfaces.

Flowers:

*Time.*—Late-season, at Almonte, Huelva, Spain, with first flower commonly at approximately January 30$^{th}$, and 50 percent bloom at approximately March 20$^{th}$.

*Number.*—Commonly approximately 7 flowers per inflorescence on average.

*Petals.*—5 in number and fused into a corolla tube.

*Corolla shape.*—Urceolate.

*Corolla size.*—The corolla tube commonly is approximately 9.8 mm in length on average, and approximately 9.1 mm in width on average at the widest point.

*Corolla color.*—Commonly near White Group 155B.

*Sepals.*—Commonly 5 in number.

*Calyx.*—Commonly approximately 3.8 mm in length on average, a basin depth of approximately 2.4 mm, and a basin diameter of approximately 7.7 mm, and the coloration commonly is Green Group 142B.

*Stamen.*—Commonly approximately 10 per flower.

*Filaments.*—Commonly non-adnate, pubescent, light green in coloration, and approximately 3.4 mm in length on average.

*Anthers.*—Bronze-colored, and the size ratio of the pollen sac:pollen tube commonly is approximately 1:1.

*Pistil.*—One per flower and light green in coloration with some slight darkening towards the base.

*Style.*—Cone-shaped in configuration, approximately 9.2 mm in length on average, and approximately 0.8 to 1 mm in thickness at the base on average.

*Peduncle.*—Commonly approximately 4.6 mm in length, approximately 1.2 mm in diameter, and the coloration is Yellow-Green Group 145B and 145C sometimes with shades of Greyed-Red Group 179B, 179C, and 179D on the upper side when exposed to the sun.

*Fertility.*—Commonly not self-fertile.

*Fragrance.*—Light.

Fruit:

*Time.*—Commonly from approximately April 30th to June 20$^{th}$ at Almonte, Huelva, Spain (i.e., approximately 7 weeks).

*Shape.*—Generally flattened-round.

*Height.*—Commonly approximately 14 mm on average.

*Width.*—Commonly approximately 22 mm on average.

*Weight.*—Approximately 3.95 g/berry on average when plants were 4 years of age.

*Firmness.*—Medium.

*Fruit scar.*—Approximately 2.3 mm in size, and relatively deep.

*Immature color.*—Commonly near Green Group 142C with bloom, and Yellow-Green Group 145A without bloom.

*Mature color.*—Light blue, Violet-Blue Group 95D with bloom, and Black Group 202A without bloom.

*Flesh color.*—Yellow-Green Group 145B and 145C.

*Productivity.*—Abundant, approximately 3.57 Kg/plant on average when plants were 4 years of age.

*Firmness.*—Medium.

*Flavor.*—Displays an aromatic sweet flavor, commonly with a fruit acidity of approximately 0.586 g/100 g.

Development:

*Ability to store.*—The fruit stores fairly well under refrigeration, when stored at 8° C. approximately 80 percent of the berries are of good quality 7 days after harvest, and when stored at 20° C. approximately 70 percent of the berries are of good quality 7 days after harvest.

*Disease tolerance.*—No special sensitivity to common Blueberry diseases. such as Leaf Rust (Pucciniastrum vaccinii) and Botrytis (Botrytis cinerea) has been encountered during observations to date at Almonte, Huelva, Spain. During observations to date the new cultivar is less susceptible to Leaf Rust than the 'Blue Crisp' cultivar, and is less resistant to Stem Blight than the 'Star' cultivar.

*Insects.*—Is susceptible to aphids and thrips.

*Cultural conditions.*—Is well suited for growing in dry climate areas outside tunnels while utilizing non-evergreen management.

*Heat resistance.*—Heat tolerant, has withstood temperatures as high as 45° C. at Almonte, Huelva, Spain.

*Cold resistance.*—Has withstood temperatures as low as −10° C. at Almonte, Huelva, Spain.

Plants of the 'Sevilla' cultivar have not been observed under all possible environmental conditions to date. Accordingly, it is possible that the phenotypic expression may vary somewhat with changes in light intensity and duration, cultural practices, and other environmental conditions without variance in the genotype.

We claim:

1. A new and distinct Blueberry plant that possesses the following combination of characteristics:

(a) flowers and forms fruit at late-season, (b) displays a open-round somewhat sprawling growth habit with attractive foliage that commonly defoliates during the winter, (c) commonly requires cross pollination for good fruit set and quality, (d) displays a low chilling requirement, and (e) forms in abundance attractive large light blue flattened-round berries that exhibit an aromatic sweet flavor;

substantially as herein shown and described.

* * * * *